(12) United States Patent
Myers et al.

(10) Patent No.: US 12,336,805 B2
(45) Date of Patent: Jun. 24, 2025

(54) SYSTEM AND METHOD FOR DETECTING AND/OR MONITORING THE PRESENCE OF AT LEAST ONE OF PNEUMOTHORAX, HEMOPNEUMOTHORAX, OR HEMOTHORAX IN A LIVING SUBJECT USING ONE OR MORE LIGHT SOURCES AND ONE OR MORE LIGHT DETECTORS

(71) Applicant: Vivonics, Inc., Bedford, MA (US)

(72) Inventors: Ryan Myers, North Andover, MA (US); Kristian DiMatteo, Waltham, MA (US); Michaelina Dupnik, Brighton, MA (US)

(73) Assignee: Vivonics, Inc., Bedford, MA (US)

( * ) Notice: Subject to any disclaimer, the term of this patent is extended or adjusted under 35 U.S.C. 154(b) by 321 days.

(21) Appl. No.: 17/577,659

(22) Filed: Jan. 18, 2022

(65) Prior Publication Data

US 2022/0225892 A1 Jul. 21, 2022

Related U.S. Application Data

(60) Provisional application No. 63/139,384, filed on Jan. 20, 2021.

(51) Int. Cl.
*A61B 5/08* (2006.01)
*A61B 5/00* (2006.01)
(Continued)

(52) U.S. Cl.
CPC .......... *A61B 5/0816* (2013.01); *A61B 5/0073* (2013.01); *A61B 5/0075* (2013.01);
(Continued)

(58) Field of Classification Search
CPC ... A61B 5/0816; A61B 5/0073; A61B 5/0075; A61B 5/02405; A61B 5/14542; A61B 5/6833; A61B 5/72
See application file for complete search history.

(56) References Cited

U.S. PATENT DOCUMENTS

| | | | |
|---|---|---|---|
| 4,838,279 A | * | 6/1989 | Fore ..................... A61B 5/1135 600/595 |
| 5,692,503 A | | 12/1997 | Kuenstner |

(Continued)

FOREIGN PATENT DOCUMENTS

| | | |
|---|---|---|
| CN | 111265287 A | 6/2020 |
| WO | 2020216839 A1 | 10/2020 |

OTHER PUBLICATIONS

Saniye et al.; "How successful is "pleural sound sign" in the identification of pneumothorax?"; North Clin Istanb 2019;6(3):273-278 (Year: 2019).*

(Continued)

*Primary Examiner* — Dixomara Vargas
(74) *Attorney, Agent, or Firm* — Iandiorio Teska & Coleman, LLP

(57) ABSTRACT

A system for detecting and/or monitoring at least one of pneumothorax, hemopneumothorax, or hemothorax using one or more light sources and one or more light detectors. The system includes one or more light sources adapted to be placed on skin of a living subject. The one or more light detectors are adapted to be placed on the skin of the living subject. A processing subsystem is coupled to the one or more light sources and the one or more light detectors detects and/or monitors the presence of at least one of pneumothorax, hemopneumothorax, or hemothorax in the living subject.

39 Claims, 7 Drawing Sheets

(51) Int. Cl.
   A61B 5/024    (2006.01)
   A61B 5/145    (2006.01)
(52) U.S. Cl.
   CPC ...... *A61B 5/02405* (2013.01); *A61B 5/14542* (2013.01); *A61B 5/6833* (2013.01); *A61B 5/72* (2013.01)

(56) References Cited

U.S. PATENT DOCUMENTS

| | | | | |
|---|---|---|---|---|
| 5,816,245 | A * | 10/1998 | Manseur | A61B 5/0059 600/407 |
| 7,831,298 | B1 * | 11/2010 | Wang | A61B 1/2676 600/478 |
| 8,073,517 | B1 * | 12/2011 | Burchman | A61B 5/14542 600/341 |
| 2004/0044276 | A1 * | 3/2004 | Arnold | A61B 5/14551 600/323 |
| 2008/0269577 | A1 * | 10/2008 | Stoddart | A61B 5/14551 600/322 |
| 2010/0198027 | A1 * | 8/2010 | Dixon | A61B 5/412 600/323 |
| 2010/0222663 | A1 | 9/2010 | Wilder et al. | |
| 2012/0130201 | A1 * | 5/2012 | Jain | A61B 5/08 600/301 |
| 2012/0215075 | A1 * | 8/2012 | Surace | A61B 5/0002 600/301 |
| 2012/0220844 | A1 * | 8/2012 | Baker, Jr. | A61B 5/0095 600/323 |
| 2013/0018240 | A1 * | 1/2013 | McCoy | A61B 5/05 600/407 |
| 2013/0172703 | A1 * | 7/2013 | Dixon | A61B 5/14551 600/339 |
| 2014/0073891 | A1 * | 3/2014 | Stoddart | A61B 5/14551 600/328 |
| 2014/0267299 | A1 * | 9/2014 | Couse | G06T 11/206 345/440.2 |
| 2014/0276048 | A1 | 9/2014 | Kiley et al. | |
| 2015/0065849 | A1 | 3/2015 | Burlina et al. | |
| 2015/0094597 | A1 | 4/2015 | Mestha et al. | |
| 2017/0273659 | A1 * | 9/2017 | Xu | G06T 7/174 |
| 2019/0156484 | A1 * | 5/2019 | Nye | G16H 30/20 |
| 2020/0222027 | A1 | 7/2020 | Xu et al. | |
| 2022/0096796 | A1 * | 3/2022 | McLaughlin | A61B 5/061 |
| 2022/0202311 | A1 * | 6/2022 | Fellman | A61B 5/0803 |
| 2022/0233119 | A1 * | 7/2022 | Shelton, IV | A61B 17/07207 |
| 2022/0241474 | A1 * | 8/2022 | Shelton, IV | A61B 5/0205 |

OTHER PUBLICATIONS

Ashraf F Hefny et al. ; "Management of computed tomography-detected pneumothorax in patients with blunt trauma: experience from a community-based hospital" ; Singapore Med J 2018; 59(3): 150-154 (Year: 2018).*

R. Kannan; "A computational model to detect and quantify a primary blast lung injury using near-infrared optical tomography" ; Wiley online library; Numerical methods in Biological Engineering, vol. 27, Issue1; Abstract (only); 2010 (Year: 2010).*

Preston et al. ; "Infrared thermography: a rapid, portable, and accurate technique to detect experimental pneumothorax"; Journal of Surgical Research 120, 163-170 (2004) (Year: 2004).*

Sheng et al.; "Chromophore concentrations, absorption and scattering properties of human skin in-vivo"; Opt Express. Aug. 17, 2009; 17(17): 14599-14617 (Year: 2009).*

Written Opinion from the International Searching Authority for International Application No. PCT/US2022/012908, dated Oct. 12, 2022, eight (8) pages.

Morris, M.J., "Acute Respiratory Distress Syndrome in Combat Casualties: Military Medicine and Advances in Mechanical Ventilation", Military Medicine, 2006. 171(11): p. 1039-1044.

King, et al., "War Wounds of the Chest Among Marine and Naval Casualties in Korea", Surgery, Gynecology & Obstetrics, 1953, 97(2): p. 199-212.

Brewer III, L.A., "The Contributions of the Second Auxiliary Surgical Group to Military Surgery During World War II with Special Reference to Thoracic Surgery", Annals of Surgery, 1983, 197(3): p. 318-326.

Trunkey, D.D., "History and Development of Trauma Care in the United States", Clinical Orthopaedics and Related Research, 2000, 374: p. 36-46.

Bagg, et al. "Levels of Medical Care in the Global War on Terrorism", JAAOS-Journal of the American Academy of Orthopaedic Surgeons, 2006, 14(10): p. S7-S9.

Eastridge, et al., "Death On The Battlefield (2001-2011): Implications for the Future of Combat Casualty Care", Journal of Trauma and Acute Care Surgery, 2012, 73(6), p. S431-S437.

Ivey, et al., "Thoracic Injuries in US Combat Casualties: A 10-Year Review of Operation Enduring Freedom and Iraqi Freedom" Journal of Trauma and Acute Care Surgery, 2012, 73(6), p. S514-S519.

Utter, G.H., "The Rate of Pleural Fluid Drainage as a Criterion for the Timing of Chest Tube Removal: Theoretical and Practical Considerations", The Annals of Thoracic Surgery, 2013, 96(6): p. 2262-2267.

Aylwin, et al., "Pre-Hospital and In-Hospital Thoracostomy: Indications and Complications", The Annals of the Royal College of Surgeons of England, 2008, 90(1): p. 54-57.

Ferrie, et al., "The Right Place in the Right Space? Awareness of Site for Needle Thoracocentesis" Emergency Medicine Journal, 2005, 22(11): p. 788-789.

Wernick, et al., "Complications of Needle Thoracostomy: A Comprehensive Clinical Review" International Journal of Critical Illness and Injury Science, 2015, 5(3): p. 160-169.

Leigh-Smith, et al., "Tension Pneumothorax—Time for a Re-Think?", Emerg. Med. J., 2005, 22(1): p. 8-16.

Sharma, et al., "Principles of Diagnosis and Management of Traumatic Pneumothorax", Journal of Emergencies, Trauma and Shock, 2008, 1(1): p. 34-41.

Prince, et al., "Monte Carlo Simulation of NIR Diffuse Reflectance in the Normal and Diseased Human Breast Tissues" Biofactors, 2007, 30(4): p. 255-263.

Tsai, et al., "A Noncontact Skin Oxygen-Saturation Imaging System for Measuring Human Tissue Oxygen Saturation" EEE Trans. on Instrumentation and Measurement, 2014. 63(11): p. 2620-2631.

Clemency, et al., "Sufficient Catheter Length for Pneumothorax Needle Decompression: A Meta-Analysis" Prehospital and Disaster Medicine, 2015, 30(3), p. 1-5.

Maruo, et al., "In Vivo Noninvasive Measurement of Blood Glucose by Near-Infrared Diffuse-Reflectance Spectroscopy", Applied Spectroscopy, 2003, 57(10): p. 1236-1244.

* cited by examiner

SYSTEM AND METHOD FOR DETECTING AND/OR MONITORING THE PRESENCE OF AT LEAST ONE OF PNEUMOTHORAX, HEMOPNEUMOTHORAX, OR HEMOTHORAX IN A LIVING SUBJECT USING ONE OR MORE LIGHT SOURCES AND ONE OR MORE LIGHT DETECTORS

RELATED APPLICATIONS

This application claims benefit of and priority to U.S. Provisional Application Ser. No. 63/139,384 filed Jan. 20, 2021 under 35 U.S.C. §§ 119, 120, 363, 365, and 37 C.F.R. § 1.55 and § 1.78, which is incorporated herein by this reference.

GOVERNMENT RIGHTS

This invention was made in part with U.S. Government support under Contract W81XWH-19-C-0112, awarded by the U.S. Army. The Government has certain rights in the invention.

FIELD OF THE INVENTION

This invention relates to a system and method for detecting and/or monitoring the presence of at least one of pneumothorax, hemopneumothorax, or hemothorax in a living subject using one or more light sources and one or more light detectors.

BACKGROUND OF THE INVENTION

Pneumothorax may be caused by a blunt or penetrating chest injury, by medical procedures, e.g., chest tube placements, or similar type procedures, or from damage to a lung from various types of lung diseases. Hemopneumothorax may also result from a blunt or penetrating chest injury when blood and air accumulate in the pleural cavity. Hemothorax is accumulation of blood in the pleural space. Typical causes of hemothorax include a laceration of the lung, a laceration of the intercostal vessel, or an internal artery. Hemothorax may also result from a blunt or penetrating chest injury.

Some conventional systems and methods to detect pneumothorax rely on using ultrasound to scan a lung of a subject. See e.g., U.S. Publ. Nos. 2020/0222027, 2017/0273659, 2014/0276048, 2013/30197370, all incorporated by reference herein. However, using ultrasound requires a large, bulky, complex, expensive device with high power requirements and is typically not readily portable.

Other conventional methods to detect pneumothorax rely on obtaining a series of frames of image data relating to a region of interest of a lung and using processing circuitry to analyze the frames of image date to determine the presence of pneumothorax. See e.g., U.S. Publ. No. 2015/0065849, incorporated by reference herein. However, the frames of image data are obtained using ultrasound, computed tomography (CT) or magnetic resonance imaging (MRI), all of which are large, bulky, complex systems with high power requirements and are not readily portable.

Another conventional system to detect pneumothorax uses a micropower impulse radar (MIR) pneumothorax detector, a processor, a handheld MIR scanner, an antenna, and circuitry that generates MIR signals and processes received echoes of the MIR signals to determine the presence of pneumothorax based on the received echoes of the MIR signals. See e.g., U.S. Publ. No. 2010/0222663, incorporated by reference herein. However, the system and method as taught in the '663 patent application request complex circuitry and a cumbersome antenna.

Yet another conventional system to detect pneumothorax relies on an evaluation unit supplied with data representing a thorax magnetic resonance (MR) exposure containing a region including at least a portion of the pleural cavity. However, magnetic resonance exposure requires a large, bulky, complex, high power system and is not readily portable.

Needle decompression (ND) is one recommended intervention for treating pneumothorax, hemopneumothorax, and hemothorax. However, needle decompression may have unacceptable rates of misdiagnosis (e.g., about 40%, See e.g., Utter, G. H., *The rate of pleural fluid drainage as a criterion for the timing of chest tube removal: theoretical and practical considerations*, The Annals of Thoracic Surgery, 96(6), p. 2262-2267 (2013), incorporated by reference herein. The determination of the correct location for needle insertion at the correct location on the intercostal space is problematic, e.g., about 40% [8-10]). See e.g., Utter, G. H., *The rate of pleural fluid drainage as a criterion for the timing of chest tube removal: theoretical and practical considerations*, The Annals of Thoracic Surgery, 96(6), p. 2262-2267 (2013), Aylwin, et al., *Pre-hospital and in-hospital thoracostomy, indications and complications*, The Annals of The Royal College of Surgeons of England, 90(1), p. 54-57 (2008) and Ferrie et al., *The right place in the right space? Awareness of site for needle thoracocentesis*. Emergency Medicine Journal, 22(11), p. 788-789 (2005), all incorporated by reference herein.

The detection and/or monitoring of pneumothorax, hemopneumothorax, or hemothorax is complicated in an ideal setting and is even more complicated in a noisy and messy environment, e.g., a combat situation, emergency medicine, field medicine, or similar type situation where multiple injuries can induce the common symptoms of the condition, e.g., chest pain, respiratory distress, tachycardia, ipsilateral decreased air entry, hypoxia, hypotension, and crackles/wheezes, See e.g., Wernick et al., *Complications of needle thoracostomy: a comprehensive clinical review*, International Journal of Critical Illness and Injury Science, 5(3), p. 160 (2015).

Thus, there is a need for a small, portable, less complex, power efficient system and method to detect and/or monitor the presence of at least one of pneumothorax, hemopneumothorax or hemothorax which can be utilized in a multitude of situations where large, bulky complex system and methods cannot be used.

SUMMARY OF THE INVENTION

In one aspect, a system for detecting and/or monitoring at least one of pneumothorax, hemopneumothorax, or hemothorax using one or more light sources and one or more light detectors is featured. The system includes one or more light sources adapted to be placed on skin of a living subject. The system also includes one or more light detectors adapted to be placed on the skin of the living subject. A processing subsystem is coupled to the one or more light sources and the one or more light detectors and configured to detect and/or monitor the presence of at least one of pneumothorax, hemopneumothorax, or hemothorax in the living subject.

In one embodiment, the one or more light sources may be configured to emit light which penetrates a thoracic cavity of the living subject at one or more predetermined penetration depths and the one or more light detectors may be configured to detect at least one of reflected light from tissue between a lung of the living subject and the skin or reflected light from the lung of the living subject and generate output signals. The processing subsystem may be responsive to the output signals and may be configured to detect and/or monitor the presence of at least one of pneumothorax, hemopneumothorax, or hemothorax based on an amount of light reflected or not reflected from the thoracic cavity. The one or more light detectors may be spaced from the one or more light sources by one or more predetermined separation distances such that the one or more light detectors detect at least one of the lights reflected from tissue between the lung and the skin of the living subject or the light reflected from the lung of the living subject and generate the output signals. The processing subsystem may be configured to generate one or more tomography curves representative of the amount of reflected light from varying penetration depths and to detect and/or monitor the presence of at least one of pneumothorax, hemopneumothorax, or hemothorax based on the shape of the one or more tomography curves. The one or more light sources may be configured to emit light into tissue of the living subject and the one or more light detectors may be configured to detect light from the tissue and generate one or more physiological output signals. The processing subsystem may be responsive to the one or more physiological output signals and may be configured to determine at least one of a respiration rate of the living subject, a tissue oxygen saturation of the living subject, blood oxygenation of the living subject, or a heart rate of the living subject. The processing subsystem may be configured to determine characteristic change in the respiration rate of the living subject to detect and/or monitor the presence of at least one of pneumothorax, hemopneumothorax, or hemothorax in the living subject. The processing subsystem may be configured to determine a characteristic change in the tissue oxygen saturation and/or blood oxygenation to detect and/or monitor the presence of at least one of pneumothorax, hemopneumothorax, or hemothorax in the living subject. The processing subsystem may be configured to determine characteristic change in the heart rate to detect and/or monitor the presence of at least one of pneumothorax, hemopneumothorax, or hemothorax in the living subject. The processing subsystem may be configured to determine a combination of at least one of a characteristic change in the respiration rate of the living subject, a characteristic change in the tissue oxygen saturation of the living subject, a characteristic change in blood oxygenation of the living subject, or a characteristic change in the heart rate of the living subject to detect and/or monitor the presence of at least one of pneumothorax, hemopneumothorax, or hemothorax in the living subject. The one or more light sources may be configured to emit light at two or more predetermined wavelengths and the one or more light detectors may be configured to generate the physiological output signals responsive to each of the two or more wavelengths for the processing subsystem to determine at least one of the respiration rate of the living subject, the tissue oxygen saturation of the living subject, the blood oxygenation of the living subject or a heart rate of the living subject. The one of the predetermined wavelengths may be configured to target oxyhemoglobin chromophores and another of the predetermined wavelengths may be configured to target deoxyhemoglobin chromophores. The one or more light sources may include near infrared spectroscopy (NIRS) light sources. The one or more light sources may be adapted to be placed above a rib of the living subject and configured to emit light into the rib of the living subject and the one or more light detectors may be adapted to be placed over the rib and configured to detect reflected light from the rib and generate one or more physiological output signals. The processing subsystem may be responsive to the one or more physiological output signals and may be configured to determine a respiration rate of the living subject. The processing subsystem may be configured to determine characteristic change in the respiration rate of the living subject to detect and/or monitor the presence of at least one of pneumothorax, hemopneumothorax, or hemothorax in the living subject. The one or more light sources may be placed over at least a portion of an intercostal space of the living subject and the one or more light detectors may be adapted to be placed over at least a portion of the intercostal space and configured to detect reflected light from the intercostal space and generate one or more physiological output signals. The processing subsystem may be responsive to the one or more physiological output signals and may be configured to determine at least one of a respiration rate of the living subject, a tissue oxygen saturation of the living subject, blood oxygenation of the living subject, or a heart rate of the living subject. The processing subsystem may be configured to determine characteristic change in the respiration rate of the living subject to detect and/or monitor the presence of at least one of pneumothorax, hemopneumothorax, or hemothorax in the living subject. The processing subsystem may be configured to determine characteristic change in the tissue oxygen saturation to detect and/or monitor the presence of at least one of pneumothorax, hemopneumothorax, or hemothorax in the living subject. The processing subsystem may be configured to determine characteristic change in the heart rate to detect and/or monitor the presence of at least one of pneumothorax, hemopneumothorax, or hemothorax in the living subject. The processing subsystem may be configured to determine at least one of a characteristic change respiration rate of the living subject, a characteristic change in the tissue oxygen saturation of the living subject, or a characteristic change in the heart rate of the living subject to detect and/or monitor the presence of at least one of pneumothorax, hemopneumothorax, or hemothorax in the living subject. The one or more light sources, the one or more light detectors, and the processing subsystem may be housed in an adhesive patch attachable to the living subject. The adhesive patch may include an outlined needle zone. The adhesive patch may be attachable to the living subject using a physiological reference point on the living subject to ensure the outlined needle zone is located at an intercostal space of the living subject for insertion of a needle to treat at least one of pneumothorax, hemopneumothorax, or hemothorax. The physiological reference point may include one of: a second intercostal space-mid clavicula line, a fourth and a fifth intercostal space-mid axillary line or the fourth and the fifth intercostal space-anterior axillary line.

The subject invention, however, in other embodiments, need not achieve all these objectives and the claims hereof should not be limited to structures or methods capable of achieving these objectives.

In another aspect, a method for detecting and/or monitoring at least one of pneumothorax, hemopneumothorax, or hemothorax using light is featured. The method includes emitting light into a human subject and detecting light reflected from the human subject to detect and/or monitor the presence of at least one of pneumothorax, hemopneumothorax, or hemothorax in the living subject.

In one embodiment, the method may include emitting light which penetrates a thoracic cavity of the living subject at one or more predetermined penetration depths and detecting at least one of reflected light from tissue between lung of the living subject and skin of the living subject or reflected light from the lung of the living subject and generating output signals. The method may include responding to the output signals and detecting and/or monitoring the presence of at least one of pneumothorax, hemopneumothorax, or hemothorax based on an amount of light reflected or not reflected from the thoracic cavity. The light emitted may be spaced by one of more predetermined separation distances to detect at least one of light reflected from tissue between the lung and the skin of the living subject or light reflected from the lung of the living subject and generating output signals. The method may include generating one or more tomography curves representative of an amount of reflected light from varying penetration depths to detect and/or monitor the presence of at least one of pneumothorax, hemopneumothorax, or hemothorax based on the shape of the one or more tomography curves. The method may include emitting light into tissue of the living subject, detecting light from the tissue, and generating one or more physiological output signals. The method may include responding to the one or more physiological output signals and determining at least one of the respiration rate of the living subject, a tissue oxygen saturation of the living subject, blood oxygenation of the living subject, or a heart rate of the living subject. The method may include determining a characteristic change in the respiration rate of the living subject to detect and/or monitor the presence of at least one of pneumothorax, hemopneumothorax, or hemothorax. The method may include determining at least one of a characteristic change in tissue oxygen saturation or blood oxygenation to detect and/or monitor the presence of at least one of pneumothorax, hemopneumothorax, or hemothorax in a living subject. The method may include determining a characteristic change in the heart rate to detect and/or monitor the presence of at least one of pneumothorax, hemopneumothorax, or hemothorax in a living subject. The method may include determining at least one of a characteristic change in the respiration rate of a living subject, a characteristic change in the tissue oxygenation saturation of a living subject, a characteristic change in blood oxygenation of a living subject, or a characteristic change in the heart rate in a living subject to detect and/or monitor the presence of at least one of pneumothorax, hemopneumothorax, or hemothorax in a living subject. The method may include emitting light at two or more predetermined wavelengths and detecting and generating the physiological output signals responsive to each of the two more wavelengths to determine at least one of the respiration rate of the living subject, the tissue oxygen saturation of the living subject, the blood oxygenation of the living subject, or the heart rate of the living subject. One of the predetermined wavelengths may be configured to target oxyhemoglobin chromophores and another of the predetermined wavelengths may be configured to target deoxyhemoglobin chromophores. The method may include emitting light into the rib of the living subject and detecting light from the rib and generating one or more physiological output signals. The method may include responding to the one or more physiological signals and determining a respiration rate of the human subject. The method may include determining a characteristic change in the respiration rate of the living subject and detecting and/or monitoring the presence of at least one of pneumothorax, hemopneumothorax, or hemothorax in the living subject. The method may include emitting light over an intercostal space of the living subject and detecting light reflected from the intercostal space and generating one or more physiological output signals. The method may include responding to the one or more physiological output signals and determining at least one of a respiration rate of the living subject, a tissue oxygenation of the living subject, blood oxygenation of the living subject, or a heart rate of the living subject. The method may include determining a characteristic change in the respiration of the living subject to detect and/or monitor the presence of at least one of pneumothorax, hemopneumothorax, or hemothorax in the living subject. The method may include determining a characteristic change in the tissue oxygen saturation to detect and/or monitor the presence of at least one of pneumothorax, hemopneumothorax, or hemothorax in the living subject. The method of may include determining at least one of a characteristic change in respiration rate of the living subject, a characteristic change in tissue oxygen saturation of the living subject, or a characteristic change in the heart rate of the living subject to detect and/or monitor the presence of at least one of pneumothorax, hemopneumothorax, or hemothorax in the living subject.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
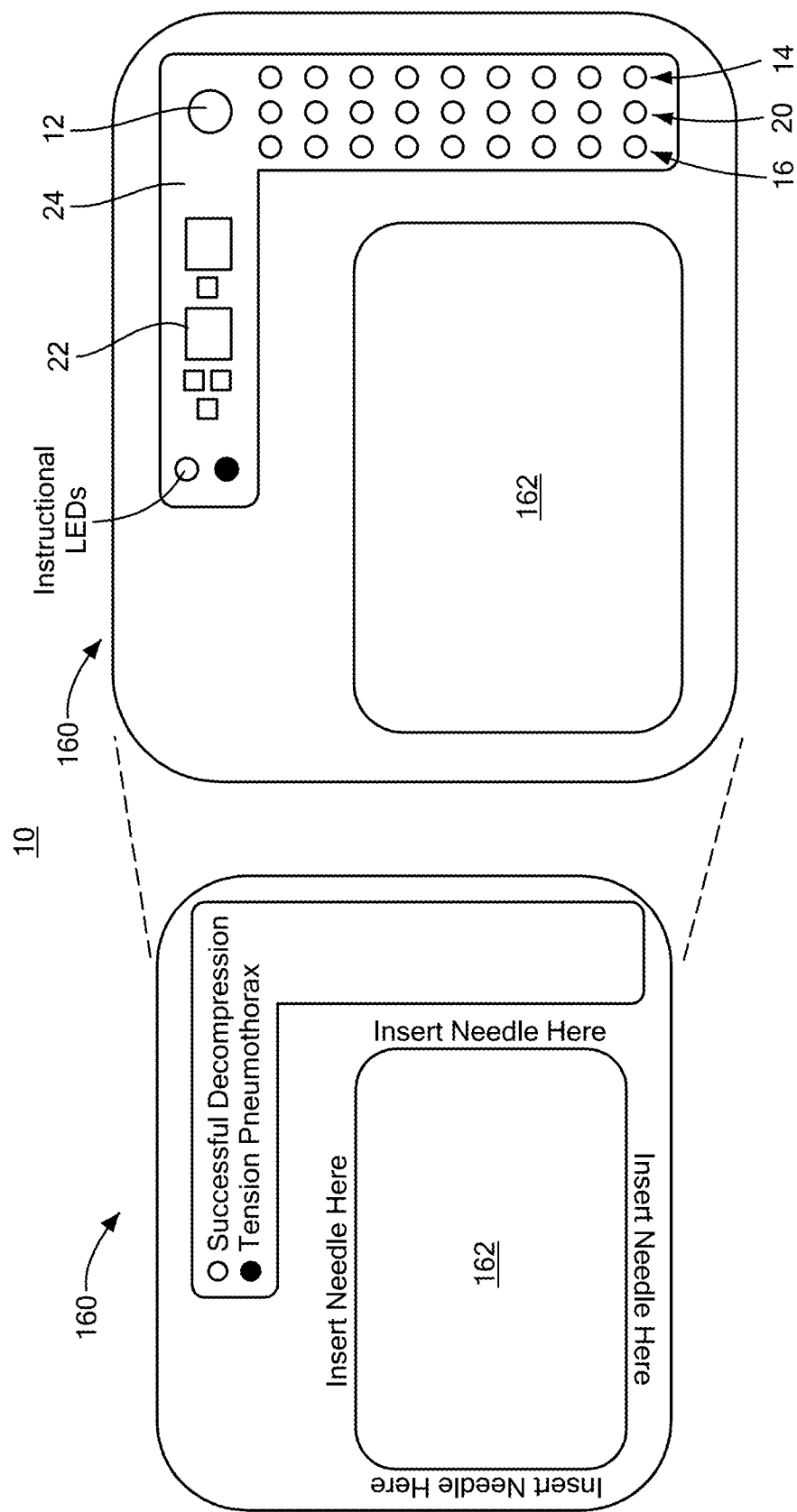
FIG. 1 is a schematic block diagram showing the primary components of one example of the system for detecting and/or monitoring at least one of pneumothorax, hemopneumothorax, or hemothorax using one or more light sources and one or more light detectors.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1, one example of system 10 for detecting and/or monitoring at least one of pneumothorax, hemopneumothorax, or hemothorax using one or more light sources and one or more light detectors. System 10 includes one or more light sources adapted to be placed on the skin of a living subject. In one design, the one or more light sources preferably includes light source 12, which in one design, is preferably configured as a high power near infrared spectroscopy (NIRS) light source which, in one example, is preferably a high power NIRS LED. In another design, the one or more light sources may include one or more light sources indicated generally at 14 and/or one or more light sources indicated generally at 16. In this example, one or more light sources 14 and/or one or more light sources 16 may include a single light source, two or more light sources, or an array of light sources as shown in FIG. 1. In this design, one or more light sources 16 and/or one or more light sources 18 are preferably NIRS light sources, as discussed in further detail below. In other examples, light source 12 and one or more light sources 14 and/or one or more light sources 16 may be other types of light sources known to those skilled in the art, e.g., a laser diode or similar type light source as known by those skilled in the art.

System 10 also includes one or more light detectors adapted to be placed the skin of a living subject, e.g., one or more light detectors indicated generally at 20. One or more light detectors 20 may include a single light detector, two or more light detectors, or an array of light detectors, e.g., as shown in FIG. 1. In one example, one or more or all of one or more light detectors 20 may include depth focus photodetectors and/or conventional light source detectors.

System 10 also includes processing subsystem 22, preferably mounted on flexible electronics board 24 which includes a power supply, a storage device, and the like, known to those skilled and the art. Processing subsystem 22 is coupled to one or more light sources 12, one or more light sources 14, one or more light sources 16, and one or more light detectors 20. Processing subsystem 22 detects and/or monitors for the presence of at least one of pneumothorax, hemopneumothorax, or hemothorax in a living subject, as discussed in detail below. As disclosed herein. "at least one of pneumothorax, hemopneumothorax, or hemothorax" may include pneumothorax and/or hemopneumothorax and/or hemothorax.

Processing subsystem 22 may include one or more processors, an application-specific integrated circuit (ASIC), firmware, hardware, and/or software (including firmware, resident software, micro-code, and the like) or a combination of both hardware and programs that may all generally be referred to herein as a "processing subsystem".

In one example, one or more light sources 12, one or more light sources 14, one or more light sources 16, and one or more light detectors 20, processing subsystem 22, and flexible electronics board 24 are preferably adapted to be placed on the skin 26, FIG. 2, of a living subject 28 preferably at location 30, as discussed in further detail below.

Figure 2:
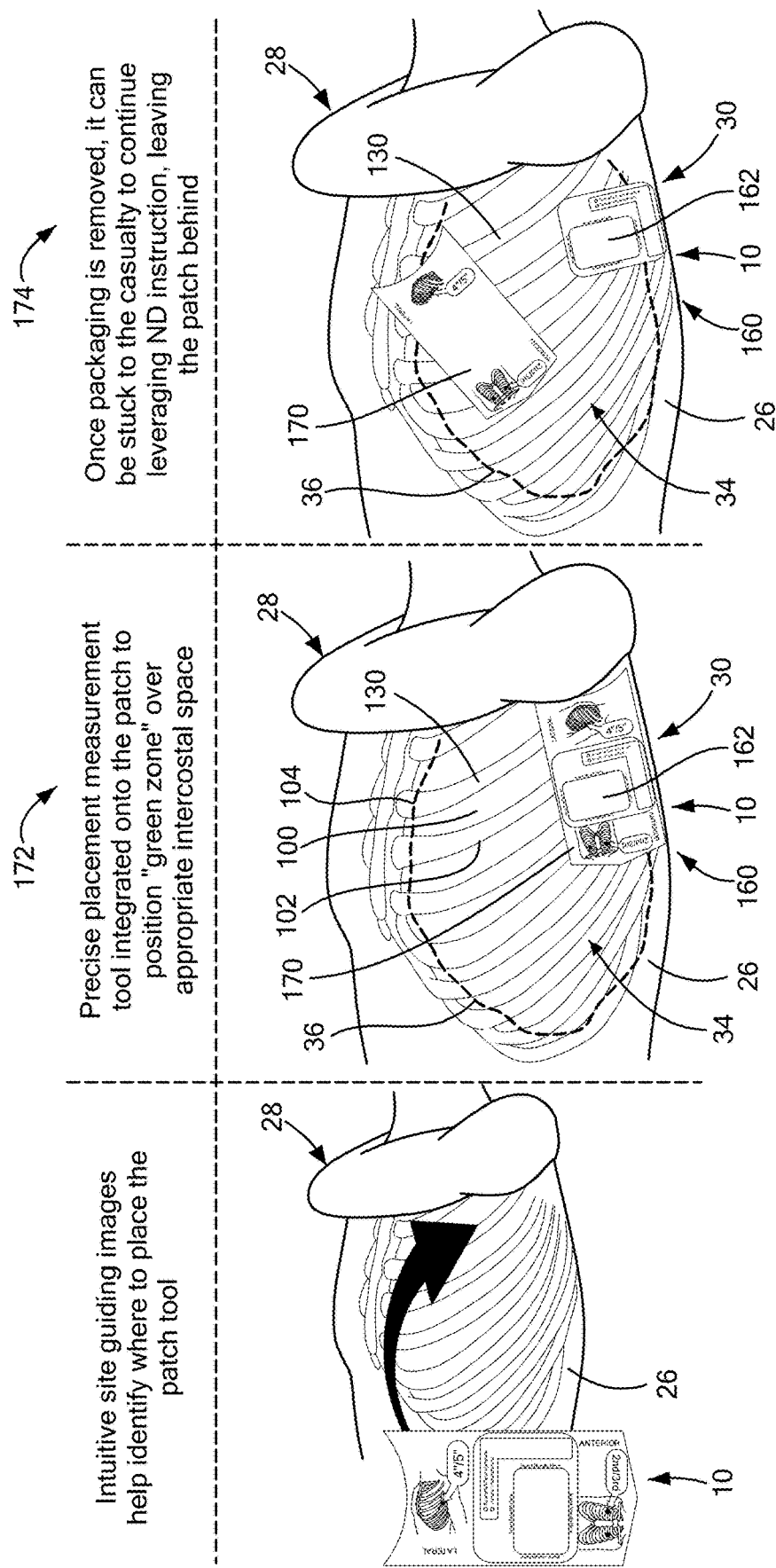
FIG. 2 shows an example of the system shown in FIG. 1 in place on the skin of a living subject at a desired location.
Figure 3:
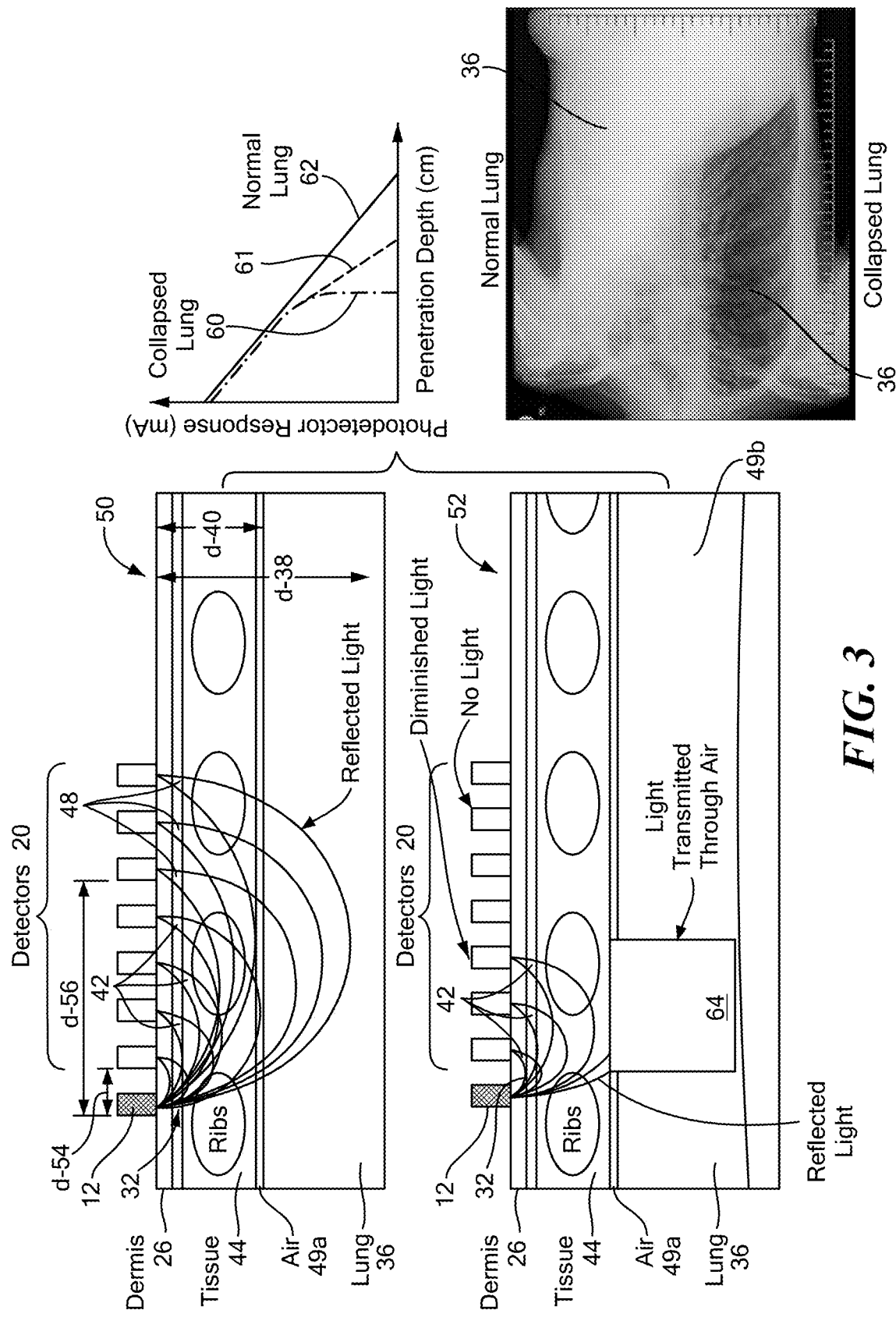
FIG. 3 shows examples of the light emitted by the one or more light sources shown in FIG. 1 and detectors detecting reflected light for a normal lung and a collapsed lung and also shows an examples of a tomography curves for light reflected from a normal lung and a collapsed lung.

In one design, one or more light sources 12, FIG. 1, emits light 32, FIG. 3, which penetrates thoracic cavity 34, FIG. 2, having lung 36 therein, shown in greater detail in FIG. 3, at one or more predetermined penetration depths, e.g., penetration depth d-38, FIG. 3, and penetration depth d-40. One or more detectors 20 detect reflected light 42 from tissue 44 between lung 36 and skin 26 and/or detect reflected light 48 reflected from lung 36 and generates output signals.

Processing subsystem 22, FIG. 1, is responsive to the output signals output by one or more light detectors 20 and detects and/or monitors the presence of at least one of pneumothorax, hemopneumothorax, or hemothorax based on the amount of light reflected or not reflected from thoracic cavity 24. For example, processing subsystem 22 detects and/or monitors the presence of at least one of pneumothorax, hemopneumothorax, or hemothorax by determining if one or more light detectors 20, FIG. 3, have detected light 48 reflected from lung 36 with the light traveling to and from lung 36 and going through thin air layer 49a which indicates a healthy lung and the absence of pneumothorax, hemopneumothorax, or hemothorax, indicated generally at 50.

Processing subsystem 22 also detects and/or monitors the presence of at least one of pneumothorax, hemopneumothorax, or hemothorax by determining if one or more light detectors 20 have detected only light 42 reflected from tissue 44 because light that passes through tissue 44 and enters wide air space 49b is not reflected until the light reaches lung 36 which is now significantly further from detectors 20 than it is normally which indicates a collapsed lung 36 and the presence of pneumothorax and/or hemopneumothorax, indicated generally at 52.

In one example, one or more light detectors 20, FIGS. 1 and 3, are preferably spaced from one or more light sources 12 by a predetermined separation distance, e.g., predetermined separation distance d-54. FIG. 3, between light source 12 and the first detector 20, such that the one or more light detectors 20 detect reflected light 42 from tissue 44 between lung 36 and skin 26 as shown and generate the output signals which are processed by processing subsystem 22, as discussed above. One or more light sources 12 are also preferably spaced from one of one or more light detectors 20 by another predetermined separation distance, e.g., predetermined separation distance d-56, such that one or more light detectors 20 detect reflected light 48 from lung 36 as shown and generate the output signals which are processed by processing subsystem 22, as discussed above.

In one design, processing subsystem 22 may generate a tomography curve representative of reflected light 42 from only tissue 44, e.g., collapsed lung tomography curve 60, and/or a tomography curve representative of reflected light 48 from lung 36 at predetermined penetration depth d-38, e.g., normal lung tomography curve 62 to determine the presence of at least one of pneumothorax, hemopneumothorax, or hemothorax.

System 10 and the method thereof preferably relies on NIRS to monitor multiple physiological changes that are caused by the onset of at least one of pneumothorax, hemopneumothorax, or hemothorax. The multiple physiological changes may include 1) the presence of air in the pleural space, 2) respiration rate (RR) and quality, 3) heart rate (HR) and quality, and 4) pulse oxygenation ($SpO_2$) levels and changes at the site. In one example, to detect the presence of air in the pleural cavity, various depths are probed by separating the one or more light sources 12, one or more light sources 14, and/or one or more light sources 16, FIGS. 1, 3, 4, e.g., an NIR light source, and one or more detectors 20 at specific distances along the skin and evaluating how much light is reflected from the one or more light sources to the one or more detectors, as discussed in detail above.

The mean angle of reflection remains somewhat constant, so the deeper the light propagates through the skin the greater the required distance between the one or more sources and the one or move light detectors to detect this light, See e.g., Clemency et al., *Sufficient catheter length for pneumothorax needle decompression: a meta-analysis*. Prehospital and Disaster Medicine, 30(3), p. 249-253 (2015), incorporated by reference herein. In addition, to reach greater distances into the skin before photons lose too much energy to return to the surface, higher source power and wavelengths are preferably emitted by one or more light sources 12, one or more light sources 14, and/or one or more light sources 16. See e.g., Clemency et al., cited supra. By understanding the wavelength, power, and separation requirements of the electronics, system 10 and the method thereof can be designed to investigate many centimeters into human tissue. Preferably, as discussed above, one or more light sources 12 are high power light sources, e.g., greater than about 30 mW and preferably provide wavelengths in the range of about 850-1000 nm. In this example, one or more light sources 12 are preferably configured as high power LED light sources and may be used to interrogate over about 8 cm into the thoracic cavity, which may be needed to address the minimum catheter length required for needle decompression success to treat at least one of pneumothorax, hemopneumothorax, or hemothorax, discussed in further detail below. See e.g., Maruo et al., *In vivo noninvasive measurement of blood glucose by near-infrared diffuse-reflectance spectroscopy*. Applied Spectroscopy, 57(10), p. 1236-1244, (2003), incorporated by reference herein. The techniques discussed above may be used to set minimum and maximum penetration depth requirements and subsequent separation distances between one or more light sources 12, one or more light sources 14, and/or one or more light sources 16 and one or more light detectors 20 to provide for a multi-detector array as shown in FIGS. 1-3 that can interrogate a linear path from the skin all the way past lung 36 as shown in FIG. 3. In so doing, characteristic detector response curves, e.g., tomography curves 60 and 62 based on penetration depth e.g., as shown in FIG. 3 can be leveraged to determine when there is constant tissue in the path of the light, indicated generally at 50, which indicates normal lung 36 or if there is a significant air gap 64, indicated generally at 52, which indicates a collapsed lung, or pneumothorax is present. This same configuration can also detect hemopneumothorax and hemothorax but in that case the characteristic curve for the case of collapsed lung due to hemopneumothorax or hemothorax will have a different change in slope creating a characteristic curve 61, between that of tomography curves 60 and 62, the slope as it departs from tomography curve 62 being related to the relative amount of air and blood in space 49b, where slopes associated with nearly all air represent pneumothorax and are represented by tomography curve 60, slopes associated with nearly all blood represent hemothorax and slopes in between are associated with a mix of air and blood and represent hemopneumothorax.

Figure 5:
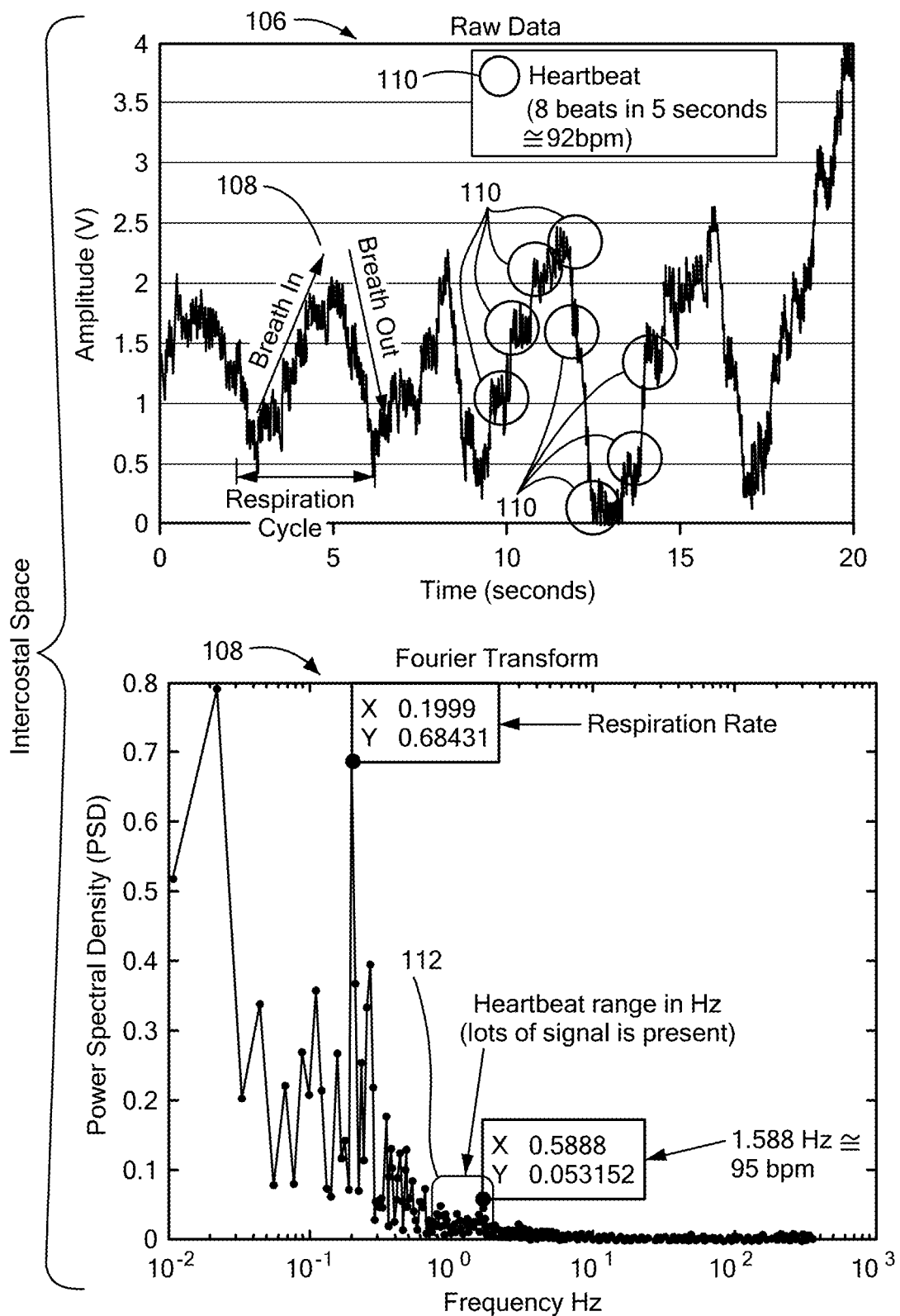
FIG. 5 shows examples of a raw data set of an intercostal space and the corresponding Fast Fourier transform utilized by the processing subsystem shown in one or more of FIGS. 1-4.

One key feature of system 10 and the method thereof is the same array of one or more light sources 12, one or more light sources 14, and/or one more light sources 16 and one or more light detectors 20 may be preferably utilized to retrieve HR, RR, and $SpO_2$. One or more light sources 12, 14, and/or 16 preferably emit light that can penetrate up to about 1.875 cm in depth to record a photoplethysmogram (PPG). As depicted in FIG. 5, a respiration cycle is shown every 5 seconds by the amplitude of the signal increasing and decreasing. If there was a tension occurring in the human subject, this oscillation would not exist. Within this waveform is a "noise," which is actually the presence of pulsatile blood flow in the intercostal space, as shown by the fast Fourier transform of the data set indicated at 108, FIG. 5. The 1.58 Hz peak seen in the Fourier transform of the data corresponds to 95 bpm (beats per minute), the heartbeat the individual was exhibiting at the time the data was collected. The recorded physiological parameters are preferably used as part of a multiparameter, machine learning (fuzzy logic-based), diagnostic to produce a highly selective and sensitive diagnostic algorithm using one or more embodiment of system 10 and the method thereof using a NIRS approach as discussed above.

The same underlying system and method can be used to distinguish a rib from an intercostal space for the purpose of making the algorithm even more intelligent. When the one of more light detectors 20 are placed over a rib, the respiration signal can still be detected, but the heartbeat frequency contribution is now absent. This heartbeat signal may be preferably utilized to provide system 10 and the method thereof with the ability to guide physicians to the proper intercostal site for needle decompression and chest tube insertion, in addition to its diagnostic capabilities. System 10. FIGS. 1-3, and the method thereof may be used regardless of the thickness of tissue between the skin and the lung because system 10 may preferably utilize tomography curves 60, 62, discussed above with reference to FIG. 3, along the detection path and need not necessarily look at a specific distance into the tissue, as typically disclosed in some conventional system and methods which may rely on ultrasound, computed tomography, and the like discussed in the Background section above. Thus, system 10 and the method thereof is preferably small, portable, light weight, fast, accurate, precise, and power efficient. Rapid diagnosis by system 10 and the method thereof also allows limits the duration of power cycling for one or more light sources 12, thus limiting temperature fluctuations and extending battery life.

In one design, one or more light sources 14, FIG. 1, and/or one or more light sources 16 preferably emit light into the tissue of living subject and one or more detectors 20 detect light from the tissue and generate one or more physiological output signals. For example, one or more or all of one or more light sources 14, e.g., light source 14, FIG. 4, may emit light 84 into tissue 36 of a living subject and/or one or more or all of one or more light sources 16, FIG. 1, e.g., light source 14, FIG. 4, may emit light 86 into tissue 36 of the living subject 28. In one design, one or more light detectors 20 preferably detect reflected light 88 from tissue 36 and/or reflected light 90 from tissue 36 to generate the one or more physiological output signals. In other designs, one or more light detectors 20' preferably detect light 94 transmitted through tissue 36 and/or detect light 96 transmitted through tissue 36 to generate the one or more physiological output signals, as discussed in further detail below.

Preferably, one or more light sources 14, and/or one or more light sources 16 are near-infrared spectroscopy (NIRS) light sources. NIRS has been used for a number of different applications in a number of different industries, primarily for its ability to penetrate mediums that visible light cannot. Near-infrared (NIR) light can be used to evaluate the oxygen saturation of the blood and other tissues, can be used to evaluate cardiac response by evaluating the photoplethysmogram (PPG) of pulsatile blood, and may be used to evaluate chemical concentrations in the blood (e.g., alcohol concentration). NIRS is powerful method of non-invasively investigating human physiology in real time can also be leveraged to detect tissue differences. Cancerous breast tissue can be differentiated from healthy breast tissue using NIRS at a modest (e.g., about 10 mW/ns pulse @ 890 nm) light output, looking up to 5 cm in depth, See e.g., Tsai et al., *A Noncontact Skin Oxygen-Saturation Imaging System for Measuring Human Tissue Oxygen Saturation*, IEEE Trans. Instrumentation and Measurement, 63(11), p. 2620-2631, incorporated by reference herein.

Figure 4:
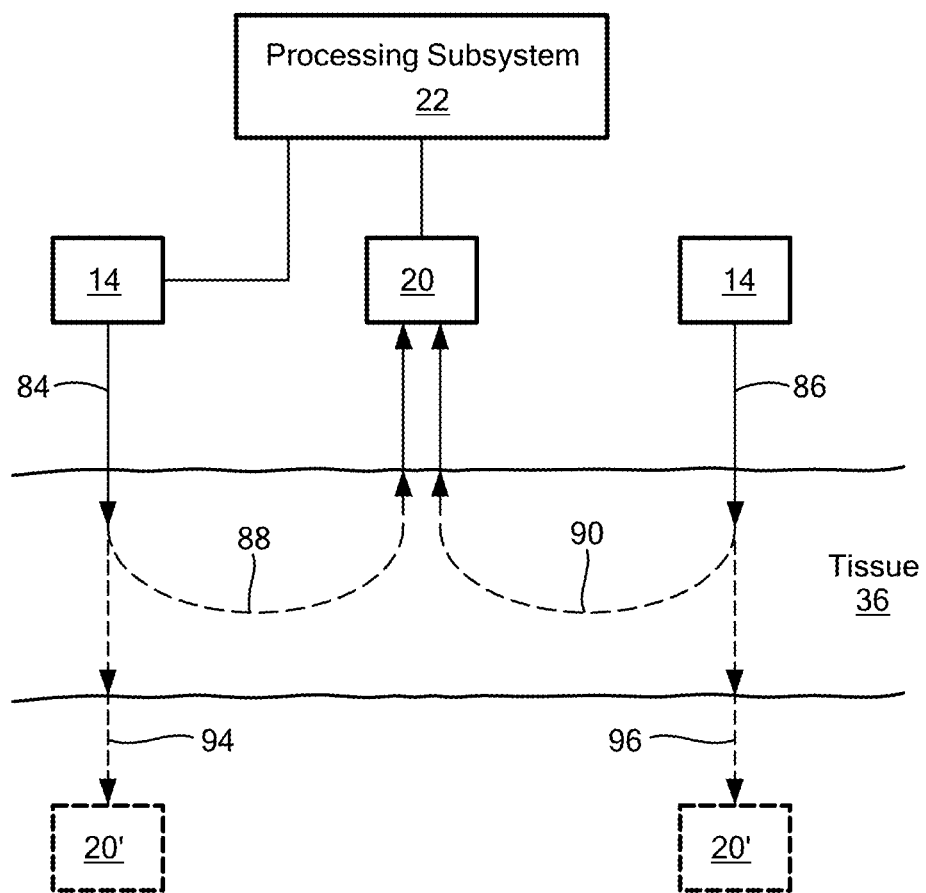
FIG. 4 is a schematic block diagram showing in further detail examples of the light emitted by one or more light sources shown in FIG. 1 and light detected by the one or more detectors for generating one or more physiological output signals.

Processing subsystem 22, FIGS. 1 and 4, is responsive to the one or more physiological output signals and determines one or more of the respiration rate of the living subject, the tissue oxygen saturation of the living subject, the blood oxygenation of the living subject and/or a heart rate of the living subject.

In one example, one of the one or more light sources 14, FIGS. 1 and 4, e.g., light source 14, FIG. 4, or one of one or more light sources 16, FIGS. 1 and 4, e.g., light source 16, FIG. 4, may be configured to emit light 84 or light 86 at two or more predetermined wavelengths. Preferably, one of the predetermined wavelengths targets oxyhemoglobin chromophores and another of the predetermined wavelengths targets deoxyhemoglobin chromophores. One of the one or more light detectors 20 preferably generates the physiological output signals in response to each of the two or more wavelengths for processing subsystem 22 to determine one or more of the respiration rate of the living subject, the tissue oxygen saturation of the living subject, the blood oxygenation of the living subject and/or a heart rate of the living subject. In this example, processing subsystem preferably alternately enables or multiplexes one of the one or more light sources 14 to emit light 84 at two or more predetermined wavelengths or one or more light sources 16 to emit light 86 at two or more predetermined wavelengths In another design, one or more of the one or more light sources 14 may be configured to emit light 84, FIG. 4, at one predetermined wavelength, e.g., about 940 nm or similar length wavelength and one or more of one or more light sources 16 may be configured to emit light 86 at another predetermined wavelength, e.g., about 660 nm or similar length wavelength. Preferably, one of the predetermined wavelengths is configured to target oxyhemoglobin chromophores and another of the predetermined wavelengths is configured to target deoxyhemoglobin. One or more of the one or more light detectors 20 preferably generates the physiological output signals in response to each of the two or more wavelengths for processing subsystem 22 to determine one or more of: the respiration rate of the living subject, the tissue oxygen saturation of the living subject, the blood oxygenation of the living subject and/or a heart rate of the living subject. In this example, processing subsystem preferably alternately enables or multiplexes one or more of one of one or more light sources 14 and one or more of one or more light sources 16 to emit light 84 at one or more predetermined wavelengths and emit light 86 at one or more predetermined wavelengths.

In one design, processing subsystem 22 may determine a characteristic change in respiration rate of the living subject, e.g., a decrease in respiration rate, to detect and/or monitor the presence of at least one of pneumothorax, hemopneumothorax, or hemothorax in the living subject. Processing subsystem 22 may also determine a characteristic change in the heart rate of the living subject, e.g., a decrease in rate to detect and/or monitor the presence of at least one of pneumothorax, hemopneumothorax, or hemothorax in the living subject. Processing subsystem 22 may also determine a characteristic change in tissue oxygen saturation and/or a characteristic change in blood oxygenation, e.g., a decrease in tissue oxygen saturation and/or blood oxygenation to detect and/or monitor the presence of at least one of pneumothorax, hemopneumothorax, or hemothorax in the living subject.

In one example, processing subsystem 22 may determine a combination of one or more or all of: a characteristic change in the respiration rate of the living subject, a characteristic change in tissue oxygen saturation of the living subject, a characteristic change in blood oxygen saturation of the living subject and/or a characteristic change in the heart rate of the living subject to detect and/or monitor the presence of at least one of pneumothorax, hemopneumothorax, or hemothorax in a living subject.

As discussed above, one or more light sources 14, FIGS. 1 and 4, and/or one or more light sources 16, preferably penetrate tissue 36, FIG. 4, and may be used to record a photoplethysmogram (PPG). In one exemplary prototype of system 10, one or more light sources 14 and one or more detectors 20 were placed over at least a portion of the intercostal space of a living subject, e.g., intercostal space 100, FIG. 2 between ribs 102 and 104 as shown. In this example, processing subsystem 22, FIGS. 1 and 4, utilized raw data set of intercostal space 100, indicated at 106, FIG. 5, and a corresponding Fast Fourier Transform, indicated at 108. Using the one or more physiological output signals discussed above generated from one or more light detectors 20, processing subsystem 22 was able to determine the respiration rate of a living subject, indicated at 108, and the heart rate of the living subject, indicated at 110. The Fourier Transform of raw data 106, indicated at 108, shows the heart beats, or heart rate, indicated by peaks 110. In this example, system 10 was able to determine a characteristic change in respiration rate of the living subject, e.g., a decrease in respiration rate, to detect and/or monitor the presence of at least one of pneumothorax, hemopneumothorax, or hemothorax in the living subject and/or determine a characteristic change in the heart rate of the living subject, e.g., a decrease in heart rate to detect and/or monitor the presence of pneumothorax and/or hemopneumothorax and/or hemothorax in the living subject, in this example, the prototype of system 10 was also able to determine a characteristic change in the tissue oxygen saturation of the living subject and/or a characteristic change in the blood oxygenation of the living subject as discussed above with reference to FIGS. 1 and 4 to detect and/or monitor the presence of at least one of pneumothorax, hemopneumothorax, or hemothorax in the living subject.

Figure 6:
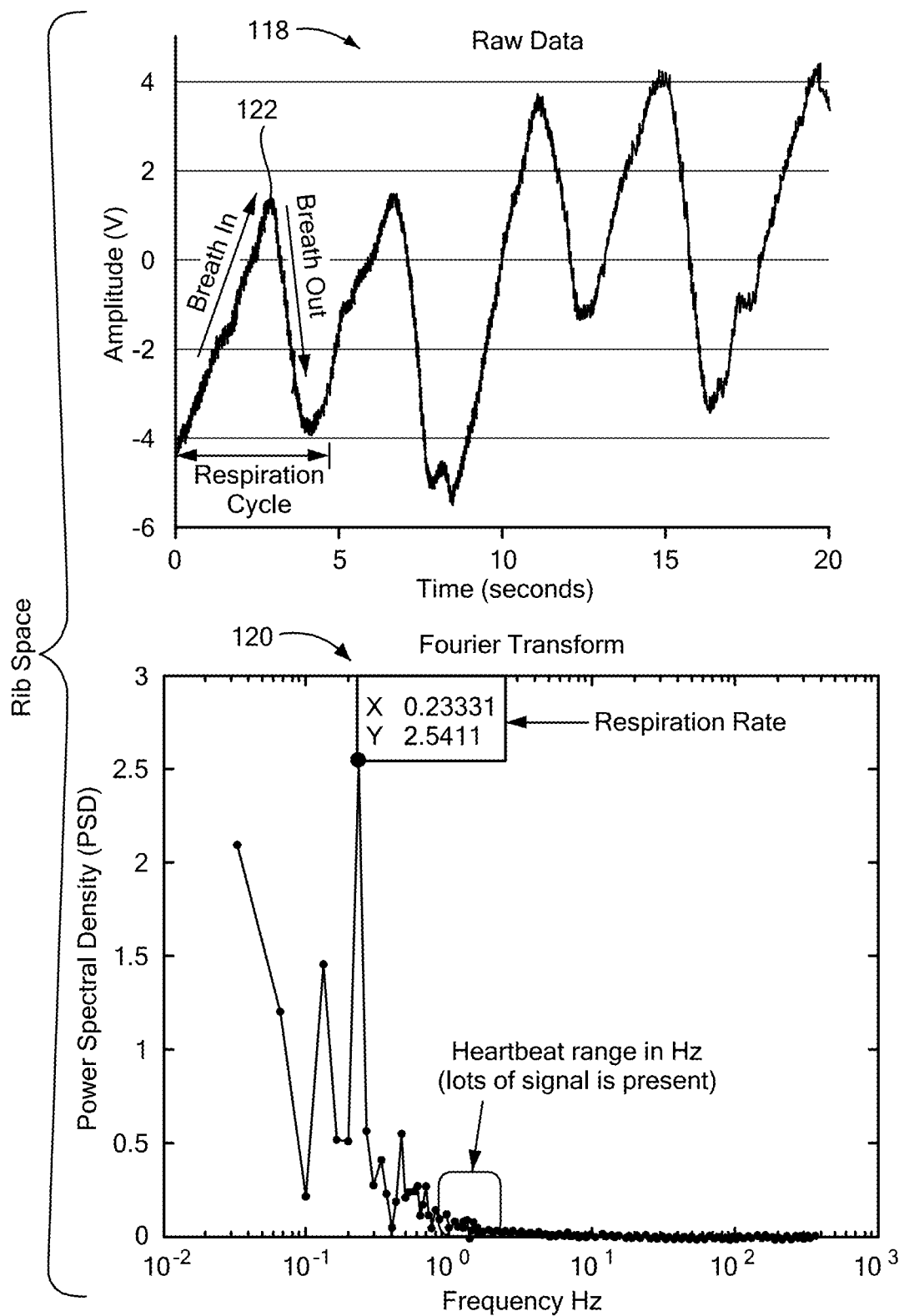
FIG. 6 shows an example of the raw data set of a rib space and the corresponding Fast Fourier transform utilized by the processing subsystem shown in one or more of FIGS. 1-5.

In another example of a prototype of system 10, one or more light sources 12 or one or more light sources 14. FIGS. 1 and 4, were placed above a rib of the living subject, e.g., rib 130, FIG. 2, of living subject 28 and the one or more light detectors 20 were placed over rib 130 and detected reflected light from the rib and generated one or more output signals. In this example, processing subsystem 22, FIGS. 1 and 4, utilized raw data set of rib space, indicated at 118, FIG. 6, and a corresponding Fast Fourier Transform, indicated at 120, Using the one or more physiological output signals discussed above generated from one or more light detectors 20, processing subsystem 22 was able to determine the respiration rate of a living subject, indicated at 122, and determine a characteristic change in the respiration rate of the living subject, e.g., a decrease in respiration rate, to detect and/or monitor the presence of at least one of pneumothorax, hemopneumothorax, or hemothorax in the living subject.

System 10 and the method thereof preferably relies on NIRS to monitor multiple physiological changes that may be caused by the onset of at least one of pneumothorax, hemopneumothorax, or hemothorax. The multiple physiological changes may include 1) the presence of air in the pleural space, 2) respiration rate (RR) and quality, 3) heart rate (HR) and quality, and 4) pulse oxygenation ($SpO_2$) levels and changes at the site. In one example, to detect the presence of air in the pleural cavity, various depths are probed by separating the one or more light sources 12, one or more light sources 14, and/or one or more light sources 16, FIGS. 1, 3, 4, e.g., an NIR light source, and one or more light detectors 20 at specific distances along the skin and evaluating how much light is reflected from the one or more light sources to the one or more light detectors, as discussed detail above. The mean angle of reflection remains somewhat constant, so the deeper the light propagates through the skin the greater the required distance between the one or more light sources and the one or more light detectors to detect this light, See e.g., Clemency et al., *Sufficient catheter length for pneumothorax needle decompression: a meta-analysis*. Prehospital and Disaster Medicine, 30(3), p. 249-253 (2015), incorporated by reference herein. In addition, to reach greater distances into the skin before photons lose too much energy to return to the surface, higher source power and wavelengths are preferably emitted by one or more light sources 12, 14, and/or 16. See e.g., Clemency et al., cited supra. By understanding the wavelength, power, and separation requirements of the electronics, system 10 and the method thereof is preferably designed to investigate many centimeters into human tissue. Preferably, as discussed above, one or more light sources 12, 14, and/or 16 are high power light sources, e.g., greater than about 30 mW and preferably provide wavelengths in the range of about 850-1000 nm. In this example, one or more light sources 12, 14, and/or 16 are preferably configured as high-power LED light sources and may be used to interrogate over about 8 cm into the thoracic cavity, which may be needed to address the minimum catheter length required for needle decompression success to treat at least one of pneumothorax, hemopneumothorax, or hemothorax, discussed in further detail below. See e.g., Maruo et al., *In vivo noninvasive measurement of blood glucose by near-infrared diffuse-reflectance spectroscopy*. Applied Spectroscopy, 57(10), p. 1236-1244, (2003), incorporated by reference herein. The techniques discussed above may be used to set minimum and maximum penetration depth requirements and subsequent separation distances between one or more light sources 12, 14, and/or 16 and one or more light detectors 20 to provide for a multi-detector array, e.g., as shown in one or more of FIGS. 1-4 that can interrogate a linear path from the skin all the way past lung 36, FIG. 3. In so doing, characteristic detector response curves, e.g., tomography curves 60 and 62 based on penetration depth can be leveraged to determine when there is constant tissue in the path of the light, indicated generally at 50, which indicates normal lung 36 or if there is a significant air gap 64, indicated generally at 52, which indicates a collapsed lung, or pneumothorax is present. This same configuration can also detect hemopneumothorax and hemothorax but in that case the characteristic curve for the case of collapsed lung due to hemopneumothorax or hemothorax will have a different change in slope creating a characteristic curve 61, between that of tomography curves 60 and 62, the slope as it departs from tomography curve 62 being related to the relative amount of air and blood in space 49*b*, where slopes associated with nearly all air represent pneumothorax and are represented by tomography curve 60, slopes associated with nearly all blood represent hemothorax and slopes in between are associated with a mix of air and blood and represent hemopneumothorax.

One key feature of system 10 and the method thereof is the same array of one or more light sources 12, 14, and/or 16 and one or more light detectors 20 may be preferably utilized to retrieve HR, RR, and $SpO_2$. One or more light sources 12, 14, and/or 16 preferably emit light that can penetrate up to about 1.875 cm in depth to record a photoplethysmogram (PPG). As depicted in FIG. 5, a respiration cycle is shown about every 5 seconds by the amplitude of the signal increasing and decreasing. If there was a tension occurring in the human subject, this oscillation would not exist. Within this waveform is a "noise," which is actually the presence of pulsatile blood flow in the intercostal space, as shown by the fast Fourier transform of the data set indicated at 108, FIG. 5. The 1.58 Hz peak seen in the Fourier transform of the data set 108 corresponds to about 95 bpm (beats per minute), the heartbeat the individual was exhibiting at the time the data was collected. The recorded physiological parameters are preferably used as part of a multiparameter, machine learning (fuzzy logic-based), diagnostic to produce a highly selective and sensitive diagnostic algorithm executed by processing subsystem 22 of system 10 and the method thereof using a NIRS approach as discussed above.

The same underlying system and method can be used to distinguish a rib from an intercostal space for the purpose of making the algorithm executed by processing subsystem 22 even more intelligent. When the one of more light detectors 20 are placed over a rib, the respiration signal can still be detected, but the heartbeat frequency contribution is now absent. This heartbeat signal may be preferably utilized to provide system 10 and the method thereof with the ability to guide physicians to the proper intercostal site for needle decompression and chest tube insertion, in addition to its diagnostic capabilities.

In one example, system 10 shown in one or more of FIGS. 1-6 may be housed in an adhesive patch and configured as adhesive patch 160, FIGS. 1 and 2, as shown, attachable to living subject 28, FIG. 2. Preferably, the adhesive patch housing system 10 includes outlined needle zone 162, FIGS. 1 and 2, attachable to living subject 18, FIG. 2, using a physiological reference point on the living subject to ensure the outlined needle zone 162 is located at the appropriate intercostal space of the living subject, e.g., intercostal space 100. FIG. 2, of living subject 28 for insertion of a needle to treat pneumothorax, hemopneumothorax, or hemothorax. In one example, the physiological reference point may include one or more of the second intercostal space-mid clavicle line, a fourth and a fifth intercostal space-mid-axillary line or a fourth and fifth intercostal space anterior line, as known by those skilled in the art.

In this example, system 10 configured as an adhesive patch is preferably a light weight, adhesive electronic patch that uses its packaging as a guide to consistently place the adhesive patch over the appropriate intercostal spaces. The adhesive patch system preferably includes an elastomer outlined needle zone 162 discussed above that identifies the needle insertion area for the user while mechanically securing the catheter once inserted. The adhesive patch system is preferably a disposable patch that may be packaged with a peel-off cover on the bottom side (similar to bandages) and a wrapper on the top that can be easily separated from the adhesive patch system after the adhesive side is applied to the skin. The wrapper serves as a measuring tool/template to help position the adhesive patch system such that outlined needle zone 162 is placed on top of the appropriate intercostal space based on a measurement from an easily identified physiologic reference point discussed above. The adhesive patch system may include scientifically validated imagery on wrapper 170, FIG. 2, for informational instructions. In operation, the user unfolds wrapper 170, removes the cover layer on the bottom side of adhesive patch system 160, then places one end of wrapper 170 at the reference point, laying the wrapper and the patch along the skin in the indicated direction, indicated at 172. This locates adhesive patch system 160 at the appropriate spot where it can be pressed down to adhere to the skin. Once the patch is adhered at the proper location, the wrapper is easily peeled from the top side of the patch, making the patch ready to use. For convenience, the user can leverage the residual adhesive on the underside of the wrapper to temporarily place the wrapper that contains clear needle decompression procedure instructions onto any surface, including the patient, for easy procedure recall, indicated at 174. Palpating through the silicone septum of outlined needle zone 162 the user can insert any needle/catheter system through outlined needle zone 162 which also doubles as a catheter securing mechanism to ensure safe transportation. This securing mechanism is similar in application to a device that has been well received by civilian paramedics, e.g., Arrow® EZ-IO® Intraosseous Vascular Access System.

In other examples, system 10 may be configured as a wand, a probe, a textile, and the like, or a combination thereof.

Figure 7:
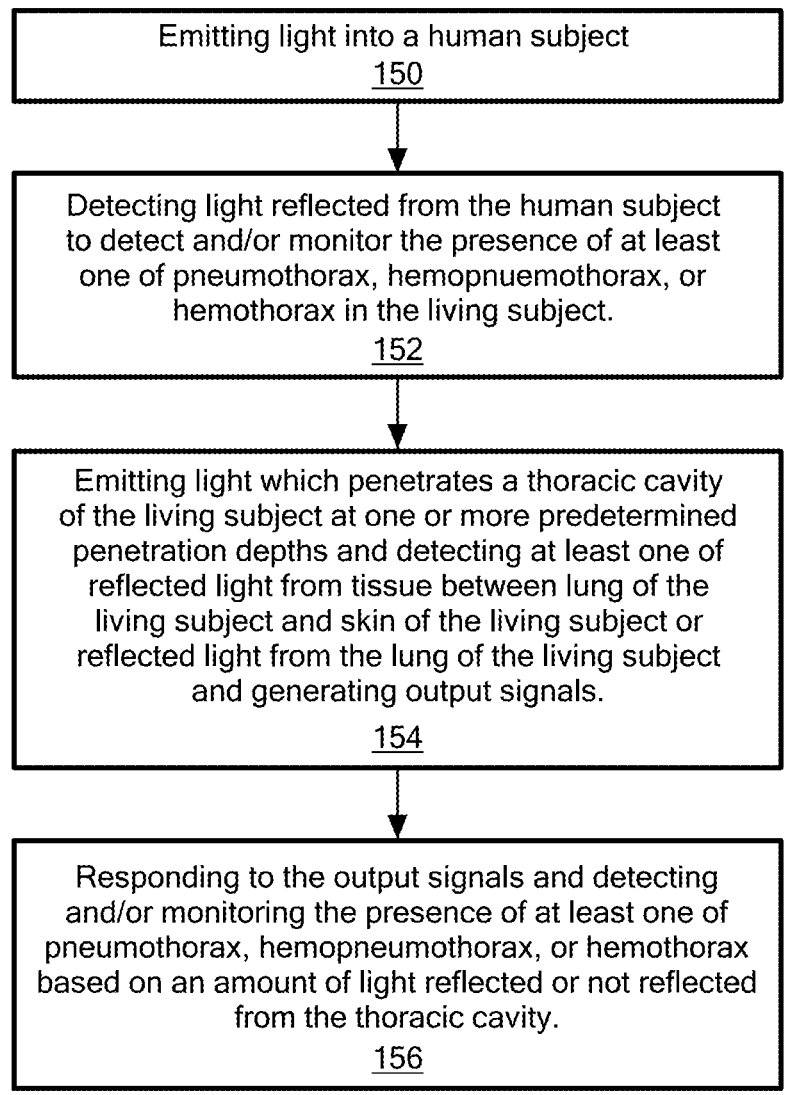
FIG. 7 is a flow chart showing one example of the method for detecting and/or monitoring at least one of pneumothorax, hemopneumothorax, or hemothorax using light.

One example for the method for detecting and/or monitoring at least one of pneumothorax, hemopneumothorax, or hemothorax using light includes emitting light into a human subject, step 150. FIG. 7, and detecting light reflected from the human subject to detect and/or monitor the presence of at least one of pneumothorax, hemopneumothorax, or hemothorax in a living subject, step 152.

In one example, the method may include emitting light which penetrates a thoracic cavity of the living subject at one or more predetermined penetration depths and detecting at least one of reflected light from the tissue between the lung of the living subject and the skin of the living subject or reflected light from the lung of a living subject and generating output signals, step 154. The method may include responding to the output signals and detecting and/or monitoring the presence of at least one of pneumothorax, hemopneumothorax, or hemothorax based on an amount of light reflected or not reflected from the thoracic cavity, step 156.

The light emitted may be spaced by one or more predetermined separation distances to detect at least one of light reflected from tissue between the lung and the skin of the living subject or light reflected from the lung of the living subject and generating output signals. The method may include generating one or more tomography curves representative of an amount of reflected light from varying penetration depths to detect and/or monitor the presence of at least one of pneumothorax, hemopneumothorax, or hemothorax based on the shape of the one or more tomography curves. The method may include emitting light into tissue of the living subject, detecting light from the tissue, and generating one or more physiological output signals. The method may include responding to the one or more physiological output signals and determining at least one of the respiration rate of the living subject, a tissue oxygen saturation of the living subject, blood oxygenation of the living subject, or a heart rate of the living subject. The method may include determining a characteristic change in the respiration rate of the living subject to detect and/or monitor the presence of at least one of pneumothorax, hemopneumothorax, or hemothorax. The method may include determining at least one of a characteristic change in tissue oxygen saturation or blood oxygenation to detect and/or monitor the presence of at least one of pneumothorax, hemopneumothorax, or hemothorax in a living subject. The method may include determining a characteristic change in the heart rate to detect and/or monitor the presence of at least one of pneumothorax, hemopneumothorax, or hemothorax in a living subject. The method of may include determining at least one of a characteristic change in the respiration rate of a living subject, a characteristic change in the tissue oxygenation saturation of a living subject, a characteristic change in blood oxygenation of a living subject, or a characteristic change in the heart rate in a living subject to detect and/or monitor the presence of at least one of pneumothorax, hemopneumothorax, or hemothorax in a living subject. The method may include emitting light at two or more predetermined wavelengths and detecting and generating the physiological output signals responsive to each of the two more wavelengths to determine at least one of the respiration rate of the living subject, the tissue oxygen saturation of the living subject, the blood oxygenation of the living subject, or the heart rate of the living subject. The method may include in which one of the predetermined wavelengths is configured to target oxyhemoglobin chromophores and another of the predetermined wavelengths is configured to target deoxyhemoglobin chromophores. The method may include emitting light into the rib of the living subject and detecting light from the rib and generating one or more physiological output signals. The method may include responding to the one or more physiological signals and determining a respiration rate of the human subject. The method may include determining a characteristic change in the respiration rate of the living subject and detecting and/or monitoring the presence of at least one of pneumothorax, hemopneumothorax, or hemothorax in the living subject. The method may include emitting light over an intercostal space of the living subject and detecting light reflected from the intercostal space and generating one or more physiological output signals. The method may include responding to the one or more physiological output signals and determining at least one of a respiration rate of the living subject, a tissue oxygenation of the living subject, blood oxygenation of the living subject, or a heart rate of the living subject. The method may include determining a characteristic change in the respiration of the living subject to detect and/or monitor the presence of at least one of pneumothorax, hemopneumothorax, or hemothorax in the living subject. The method may include determining a characteristic change in the tissue oxygen saturation to detect and/or monitor the presence of at least one of pneumothorax, hemopneumothorax, or hemothorax in the living subject. The method of may include determining at least one of a characteristic change in respiration rate of the living subject, a characteristic change in tissue oxygen saturation of the living subject, or a characteristic change in the heart rate of the living subject to detect and/or monitor the presence of at least one of pneumothorax, hemopneumothorax, or hemothorax in the living subject.

The result is system 10 shown in one or more of FIGS. 1-7 provides a robust, compact, small, accurate, precise, reliable, and power efficient system and method that effectively and accurately detects and/or monitors the presence of pneumothorax and/or hemopneumothorax and/or hemothorax in a living subject.

For enablement purposes only, the following code portions are provided which can be executed on one or more processors, a computing device, a computer, a smart device, or similar type device to carry out the primary steps and/or functions of the system and method for detecting and/or monitoring at least one of pneumothorax, hemopneumothorax, or hemothorax using one or more light sources and one or more light detectors discussed above with reference to one or more of FIGS. 1-7. Other equivalent algorithms and code can be designed by a software engineer and/or programmer skilled in the art using the information provided herein:

```
%Acquire Lung Presence Sensor 1 signal
Get(Sig_LUNG_1)
%Acquire Lung Presence Sensor 2 signal
Get(Sig_LUNG_2)
%Acquire Lung Presence Sensor 3 signal
Get(Sig_LUNG_3)
%Acquire Lung Presence Sensor 4 signal
Get(Sig_LUNG_4)
%Acquire SpO2 Sensor 1 signal
Get(Sig_OX_1)
%Acquire SpO2 Sensor 2 signal
Get(Sig_OX_2)
%Acquire SpO2 Sensor 3 signal
Get(Sig_OX_3)
%Basic Data Conditioning of acquired signals
Detrend_Sig_LUNG_1 = Det(Sig_LUNG_1)
Detrend_Sig_LUNG_2 = Det(Sig_LUNG_2)
Detrend_Sig_LUNG_3 = Det(Sig_LUNG_3)
Detrend_Sig_LUNG_4 = Det(Sig_LUNG_4)
Detrend_Sig_OX_1 = Det(Sig_OX_1)
Detrend_Sig_OX_2 = Det(Sig_OX_2)
Detrend_Sig_OX_3 = Det(Sig_OX_3)
%Perform Frequency Domain Analysis of SpO2:
PSD_OX_1 = fft(Detrend_Sig_OX_1)
PSD_OX_2 = fft(Detrend_Sig_OX_2)
PSD_OX_3 = fft(Detrend_Sig_OX_3)
%Identify Frequency Components of interest (to determine heart rate
and respiration rate)
Filt_OX_1 = FilterAtSpecificFreq (Detrend_Sig_OX_1)
Filt_OX_2 = FilterAtSpecificFreq (Detrend_Sig_OX_2)
Filt_OX_3 = FilterAtSpecificFreq (Detrend_Sig_OX_3)
%Identify SpO2 of each signal
SpO2_OX_1 = SpO2_Lookup (Detrend_Sig_OX_1)
SpO2_OX_2 = SpO2_Lookup (Detrend_Sig_OX_2)
SpO2_OX_3 = SpO2_Lookup (Detrend_Sig_OX_3)
%Use Depth Signals to determine Presence of Lung
Lung_Present == True
If (Detrend_Sig_LUNG_1>0 && Detrend_Sig_LUNG_2>0 &&
Detrend_Sig_LUNG_3>0 && Detrend_Sig_LUNG_4>0)
Else (Lung_Present == False)
%Use All Signals to determine Pneumothorax
Pneumo_Present == True
If (LungPresent == True && Average_Respiration < 2 &&
Average_HeartRate < 30 && Average_SpO2 < 85)
Else (Pneumo_Presnt == False)
%Use All Signals to determine Peumothorax in a weighted format
Pneumo_Present == True
If (WeightedLungPresent == True && WeightedAverage_Respiration < 2
&& WeightedAverage_HeartRate < 30 && WeightedAverage_SpO2 <
85)
Else (Pneumo_Presnt == False)
```

% The above is an example
% several methods may be used to combine these different signals to reach a conclusion of detecting and/or monitoring the presence of at least one of pneumothorax, hemopneumothorax, or hemothorax in a living subject using one or more light sources and one or more light detectors as discussed above.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. A system for detecting and/or monitoring at least one of pneumothorax, hemopneumothorax, or hemothorax using one or more light sources and one or more light detectors, the system comprising:
   one or more light sources adapted to be placed on skin of a living subject;
   one or more light detectors adapted to be placed on the skin of the living subject;
   the one or more light sources are configured to emit light into tissue of the living subject and the one or more light detectors are configured to detect light from the tissue and generate one or more physiological output signals, the one or more light sources configured to emit light at two or more predetermined wavelengths and the one or more light detectors configured to generate the physiological output signals responsive to the two or more wavelengths, wherein one of the predetermined wavelengths is configured to target oxyhemoglobin chromophores and another of the predetermined wavelengths is configured to target deoxyhemoglobin chromophores;
   a processing subsystem coupled to the one or more light sources and the one or more light detectors, the processing subsystem responsive to the one or more physiological output signals and configured to detect and/or monitor the presence of at least one of pneumothorax, hemopneumothorax, or hemothorax in the living subject; and wherein the one or more light sources, the one or more light detectors, and the processing subsystem are housed in an adhesive patch attachable to the living subject and the adhesive patch includes an outlined needle zone, the adhesive patch attachable to the living subject using a physiological reference point on the living subject to ensure the outlined needle zone is located at an intercostal space of the living subject for insertion of a needle to treat at least one of pneumothorax, hemopneumothorax, or hemothorax.

2. The system of claim 1 in which the one or more light sources are configured to emit light which penetrates a thoracic cavity of the living subject at one or more predetermined penetration depths and the one or more light detectors are configured to detect at least one of reflected light from tissue between a lung of the living subject and the skin or reflected light from the lung of the living subject and generate output signals.

3. The system of claim 2 in which the processing subsystem is responsive to the output signals and is configured to detect and/or monitor the presence of pneumothorax, hemopneumothorax, or hemothorax based on an amount of light reflected or not reflected from the thoracic cavity.

4. The system of claim 2 in which the one or more light detectors are spaced from the one or more light sources by one or more predetermined separation distances such that the one or more light detectors detect at least one of the light reflected from tissue between the lung and the skin of the living subject or light reflected from the lung of the living subject and generate the output signals.

5. The system of claim 4 in which the processing subsystem is configured to generate one or more tomography curves representative of the amount of reflected light from varying penetration depths and to detect and/or monitor the presence of pneumothorax, hemopneumothorax, or hemothorax based on the shape of the one or more tomography curves.

6. The system of claim 1 in which the processing subsystem is responsive to the one or more physiological output signals and is configured to determine at least one of a respiration rate of the living subject, a tissue oxygen saturation of the living subject, blood oxygenation of the living subject, or a heart rate of the living subject.

7. The system of claim 6 in which the processing subsystem is configured to determine characteristic change in the respiration rate of the living subject to detect and/or monitor the presence of at least one of pneumothorax, hemopneumothorax, or hemothorax in the living subject.

8. The system of claim 6 in which the processing subsystem is configured to determine at least one of a characteristic change in the tissue oxygen saturation or blood oxygenation to detect and/or monitor the presence of at least one of pneumothorax, hemopneumothorax, or hemothorax in the living subject.

9. The system of claim 6 in which the processing subsystem is configured to determine characteristic change in the heart rate to detect and/or monitor the presence of at least one of pneumothorax, hemopneumothorax, or hemothorax in the living subject.

10. The system of claim 6 in which the processing subsystem is configured to determine at least one of a characteristic change in the respiration rate of the living subject, a characteristic change in the tissue oxygen saturation of the living subject, a characteristic change in blood oxygenation of the living subject, or a characteristic change in the heart rate of the living subject to detect and/or monitor the presence of at least one of pneumothorax, hemopneumothorax, or hemothorax in the living subject.

11. The system of claim 1 in which the one or more light sources include near infrared spectroscopy (NIRS) light sources.

12. The system of claim 1 in which the one or more light sources are adapted to be placed above a rib of the living subject and configured to emit light into the rib of the living subject and the one or more light detectors are adapted to be placed over the rib and configured to detect reflected light from the rib and generate one or more physiological output signals.

13. The system of claim 12 in which the processing subsystem is responsive to the one or more physiological output signals and is configured to determine a respiration rate of the living subject.

14. The system of claim 13 in which the processing subsystem is configured to determine characteristic change in the respiration rate of the living subject to detect and/or monitor the presence of at least one of pneumothorax, hemopneumothorax, or hemothorax in the living subject.

15. The system of claim 1 in which the one or more light sources are placed over at least a portion of an intercostal space of the living subject and the one or more light detectors are adapted to be placed over at least a portion of the intercostal space and configured to detect reflected light from the intercostal space and generate one or more physiological output signals.

16. The system of claim 15 in which the processing subsystem is responsive to the one or more physiological output signals and is configured to determine at least one of a respiration rate of the living subject, a tissue oxygen saturation of the living subject, blood oxygenation of the living subject, or a heart rate of the living subject.

17. The system of claim 16 in which the processing subsystem is configured to determine characteristic change in the respiration rate of the living subject to detect and/or monitor the presence of at least one of pneumothorax, hemopneumothorax, or hemothorax in the living subject.

18. The system of claim 16 in which the processing subsystem is configured to determine characteristic change in the tissue oxygen saturation to detect and/or monitor the presence of at least one of pneumothorax, hemopneumothorax, or hemothorax in the living subject.

19. The system of claim 16 in which the processing subsystem is configured to determine characteristic change in the heart rate to detect and/or monitor the presence of at least one of pneumothorax, hemopneumothorax, or hemothorax in the living subject.

20. The system of claim 16 in which the processing subsystem is configured to determine at least one of a characteristic change in respiration rate of the living subject, a characteristic change in the tissue oxygen saturation of the living subject, and/or a characteristic change in the heart rate of the living subject to detect and/or monitor the presence of at least one of pneumothorax, hemopneumothorax, or hemothorax in the living subject.

21. The system of claim 1 in which the physiological reference point includes at least one of a second intercostal space-mid clavicula line, a fourth and a fifth intercostal space-mid axillary line, or the fourth and the fifth intercostal space-anterior axillary line.

22. A method for detecting and/or monitoring at least one of pneumothorax, hemopneumothorax, or hemothorax using light, the method comprising:
   emitting light into tissue of a human subject;
   detecting light reflected from the tissue of the human subject;
   generating one or more physiological output signals;
   emitting light at two or more predetermined wavelengths and detecting and generating the physiological output signals responsive to each of the two more wavelengths, wherein one of the predetermined wavelengths is configured to target oxyhemoglobin chromophores and another of the predetermined wavelengths is configured to target deoxyhemoglobin chromophores;
   responding to the one or more physiological output signal to detect and/or monitor the presence of at least one of pneumothorax, hemopneumothorax, or hemothorax in the living subject and providing one or more light sources, one or more light detectors, and a processing subsystem housed in an adhesive patch attachable to the living subject and the adhesive patch includes an outlined needle zone, the adhesive patch attachable to the living subject using a physiological reference point on the living subject to ensure the outlined needle zone is located at an intercostal space of the living subject for insertion of a needle to treat at least one of pneumothorax, hemopneumothorax, or hemothorax.

23. The method of claim 22 including emitting light which penetrates a thoracic cavity of the living subject at one or more predetermined penetration depths and detecting at least one of reflected light from tissue between lung of the living subject and skin of the living subject or reflected light from the lung of the living subject and generating output signals.

24. The method of claim 23 including responding to the output signals and detecting and/or monitoring the presence of at least one of pneumothorax, hemopneumothorax, or hemothorax based on an amount of light reflected or not reflected from the thoracic cavity.

25. The method of claim 23 in which the light emitted is spaced by one of more predetermined separation distances to detect at least one of light reflected from tissue between the lung and the skin of the living subject or light reflected from the lung of the living subject and generating output signals.

26. The method of claim 25 including generating one or more tomography curves representative of an amount of reflected light from varying penetration depths to detect and/or monitor the presence of at least one of pneumothorax, hemopneumothorax, or hemothorax based on the shape of the one or more tomography curves.

27. The method of claim 22 including responding to the one or more physiological output signals and determining at least one of the respiration rate of the living subject, a tissue oxygen saturation of the living subject, blood oxygenation of the living subject, or a heart rate of the living subject.

28. The method of claim 27 including determining a characteristic change in the respiration rate of the living subject to detect and/or monitor the presence of at least one of pneumothorax, hemopneumothorax, or hemothorax.

29. The method of claim of 28 including determining at least one of a characteristic change in tissue oxygen saturation or blood oxygenation to detect and/or monitor the presence of at least one of pneumothorax, hemopneumothorax, or hemothorax in a living subject.

30. The method of claim 27 including determining a characteristic change in the heart rate to detect and/or monitor the presence of at least one of pneumothorax, hemopneumothorax, or hemothorax in a living subject.

31. The method of claim 27 including determining at least one of a characteristic change in the respiration rate of a living subject, a characteristic change in the tissue oxygenation saturation of a living subject, a characteristic change in blood oxygenation of a living subject, or a characteristic change in the heart rate in a living subject to detect and/or monitor the presence of at least one of pneumothorax, hemopneumothorax, or hemothorax in a living subject.

32. The method of claim 22 including emitting light into the rib of the living subject and detecting light from the rib and generating one or more physiological output signals.

33. The method of claim 32 including responding to the one or more physiological signals and determining a respiration rate of the human subject.

34. The method of claim 33 including determining a characteristic change in the respiration rate of the living subject and detecting and/or monitoring the presence of at least one of pneumothorax, hemopneumothorax, or hemothorax in the living subject.

35. The method of claim 22 including emitting light over an intercostal space of the living subject and detecting light reflected from the intercostal space and generating one or more physiological output signals.

36. The method of claim 35 including responding to the one or more physiological output signals and determining at least one of a respiration rate of the living subject, a tissue oxygenation of the living subject, blood oxygenation of the living subject, or a heart rate of the living subject.

37. The method of claim 36 including determining a characteristic change in the respiration of the living subject to detect and/or monitor the presence of at least one of pneumothorax, hemopneumothorax, or hemothorax in the living subject.

38. The method of claim 36 including determining a characteristic change in the tissue oxygen saturation to detect and/or monitor the presence of at least one of pneumothorax, hemopneumothorax, or hemothorax in the living subject.

39. The method of claim 36 including determining at least one of a characteristic change in respiration rate of the living subject, a characteristic change in tissue oxygen saturation of the living subject, or a characteristic change in the heart rate of the living subject to detect and/or monitor the presence of at least one of pneumothorax, hemopneumothorax, or hemothorax in the living subject.

* * * * *